United States Patent
Welsh et al.

(10) Patent No.: US 8,188,128 B2
(45) Date of Patent: May 29, 2012

(54) OPIOID RECEPTOR SUBTYPE-SELECTIVE AGENTS

(75) Inventors: William J. Welsh, Princeton, NJ (US); Youyi Peng, Piscataway, NJ (US); Qiang Zhang, Piscataway, NJ (US); Susan M. Keenan, Franklin Park, NJ (US); Sonia Arora, Howell, NJ (US)

(73) Assignee: The University of Medicine and Dentistry of New Jersey, Somerset, NJ (US)

( * ) Notice: Subject to any disclaimer, the term of this patent is extended or adjusted under 35 U.S.C. 154(b) by 591 days.

(21) Appl. No.: 11/914,231

(22) PCT Filed: May 12, 2006

(86) PCT No.: PCT/US2006/018576
§ 371 (c)(1),
(2), (4) Date: Nov. 10, 2008

(87) PCT Pub. No.: WO2006/124687
PCT Pub. Date: Nov. 23, 2006

(65) Prior Publication Data
US 2009/0181998 A1     Jul. 16, 2009

Related U.S. Application Data

(60) Provisional application No. 60/680,259, filed on May 12, 2005.

(51) Int. Cl.
*A61K 31/4196* (2006.01)
*C07D 249/08* (2006.01)

(52) U.S. Cl. .................................... 514/383; 548/269.4

(58) Field of Classification Search .................. None
See application file for complete search history.

(56) References Cited

U.S. PATENT DOCUMENTS

| 4,259,504 A | 3/1981 | Lang, Jr. et al. |
| 4,902,805 A | 2/1990 | Shida et al. |
| 2003/0225072 A1 | 12/2003 | Welsh et al. |

FOREIGN PATENT DOCUMENTS

| HU | 195791 B | * | 7/1988 |
| WO | WO 03055875 A1 | * | 7/2003 |

OTHER PUBLICATIONS

Grant & Hackh's Chemical Dictionary, 5th ed. McGraw-Hill, Inc., p. 177 (1987).*
Byrn et al. Solid-State Chemistry of Drugs, 2d, Chapter 11 Hydrates and Solvates, 233-247 (1999).*
Morissette et al., Adv. Drug Delivery Rev., 56:275 (2004).*
A.M. Rouhi, Chem. & Eng. News, 81:32 (Feb. 24, 2003).*
Schafer et al. Drug Discovery Today, 13:913 (2008).*
Horig et al. Journal of Translational Medicine, 2:44 (2004).*
Zhang, et al. J. Med. Chem. 49:4044 (Jun. 21, 2006).*
Jutkiewicz, E.M., Molecular Interventions, 6:162 (Jun. 1, 2006).*
E.J. Bilsky et al., "SNC 80 Selective, Nonpeptidic and Systemically Active Opioid Delta Agonist", J. Pharmacol. Exp. Ther., 273, 359-365 (1995).
E.E. Abdelhamid et al., "Selective Blockage of Delta Opioid Receptors Prevents the Development of Morphine Tolerance and Dependence in Mice", J. Pharmacol. Exp. Ther., 258, 299-303 (1991).
R.V. House et al., "Suppression of Immune Function by Non-Peptidic Delta Opioid Receptor Antagonists", Neurosci. Lett., 198, 119-122 (1995).
Bozo et al., "New 1,5-Diaryl-3-(substituted amino)-1H-1,2,4-triazoles as Anti-Inflammatory Agents", Archiv der Pharmazie, vol. 322 (10), 583-587 (1989).
Liebscher et al., "About Nitrile-Formamide-Chloride-Adducts," Journal Fuer Proktische Chemie (Leipzig), 326(2), 311-319 (1984).

* cited by examiner

*Primary Examiner* — Yong Chu
*Assistant Examiner* — Michael Barker
(74) *Attorney, Agent, or Firm* — Fox Rothschild LLP

(57) ABSTRACT

Opioid receptor compounds and pharmaceutical compositions thereof are presented. Also presented are methods for treating a condition mediated by an opioid receptor by administering an effective amount of the opioid receptor compound to a patient in need thereof.

8 Claims, 1 Drawing Sheet

Figure 1. Representative competition curve of DOP108 at the δ opioid receptor.
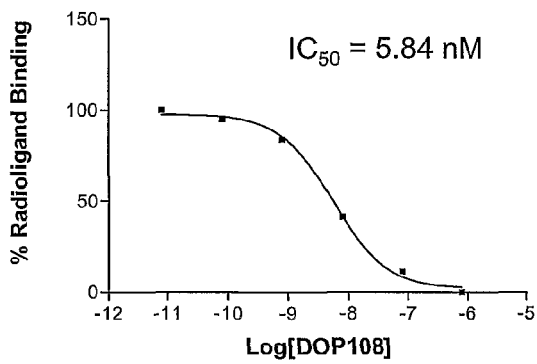
Figure 2. Effect of compounds of Formula I on activity of delta receptors. Receptor down-regulation of DOPs 6, 8, and 10 with SNC-80 and Naloxone as agonist and antagonist controls, respectively.
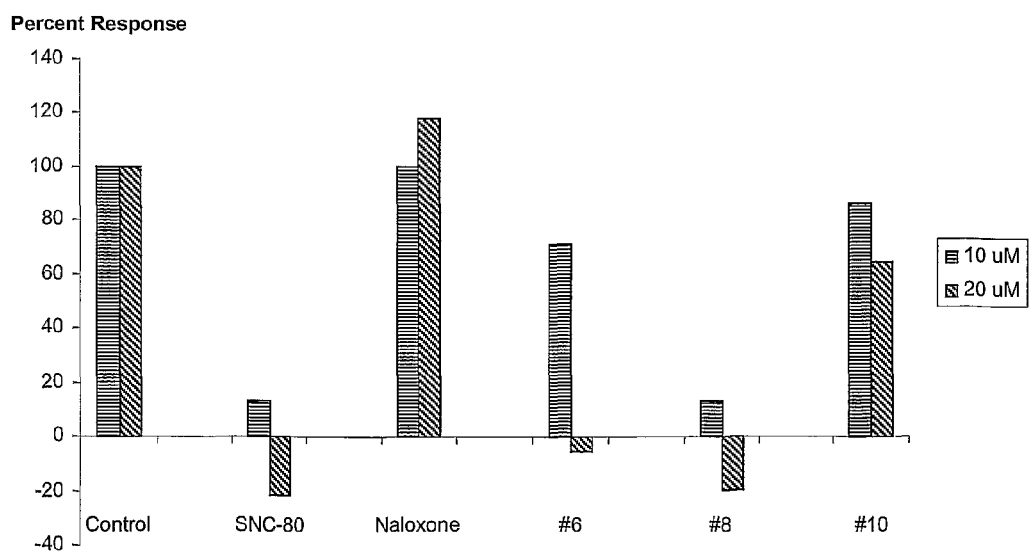

OPIOID RECEPTOR SUBTYPE-SELECTIVE AGENTS

CROSS-REFERENCE TO RELATED APPLICATIONS

This application is a National Stage of International Application No. PCT/US2006/018576, filed May 12, 2006, which claims priority under 35 U.S.C. §119(e) to U.S. Provisional Application Ser. No. 60/680,259, which was filed on May 12, 2005. The disclosures of both of which are incorporated herein by reference.

BACKGROUND OF THE INVENTION

Among the three classes of opioid receptor subtypes, designated delta (δ), kappa (κ), and mu (μ), a substantial body of evidence suggests that subtype-selective opioid receptor agents and mixed agonists-antagonists exhibit pharmacologically relevant effects. Of particular relevance in the present instance, δ-selective opioids are potentially useful as analgesics devoid of the numerous side effects (e.g., respiratory depression, physical dependence and gastrointestinal effects) associated with narcotics such as morphine (E. J. Bilsky et al., J. Pharmacol. Exp. Ther., 273, 359 (1995)). Moreover, selective antagonists of δ receptors have been shown to modulate the development of tolerance and dependence to μ agonists such as morphine (E. E. Abdelhamid et al., J. Pharmacol. Exp. Ther., 258, 299 (1991)), to modulate the behavioral effects of drugs of abuse such as cocaine (L. D. Reid et al., Life Sci., 52, PL67 (1993)), and to elicit favorable immunomodulatory effects (R. V. House et al., Neurosci. Lett., 198, 119 (1995)). The δ-selective opioids thus represent extremely attractive candidates for a broad range of novel pharmaceutical applications including powerful yet safe analgesics, immunomodulatory agents for treating immune disorders, and new treatments for drug addiction. Likewise, agents acting alone or in combination with mixed agonist-antagonist activity among the opioid receptor subtypes remain the subject of intense interest and research in the pharmaceutical industry.

Opioid narcotics can be potent painkillers, but they are also addictive. The delta (δ) receptors, along with the related kappa (κ) and mu (μ) receptors, are found on cells located throughout the central and peripheral nervous system. The receptors normally bind with opioid peptides (e.g., enkephalins) that the body produces. By binding to the receptors, these peptides modulate endocrine, cardiovascular respiratory, gastrointestinal, and immune functions. Opioid narcotics are alkaloids, with molecular structures quite distinct from opioid peptides. However, the narcotic drugs and opioid peptides share common structural features (known as pharmacophores) that enable the drugs to bind to the opioid receptors. When they bind to these receptors, the narcotics exert various effects on the perception of pain, consciousness, motor control, mood, and autonomic function. They also induce physical dependence. However, recently published studies demonstrate that compounds, or combinations of compounds, that act in concert as selective μ agonists and δ antagonists (mixed μ/δ agonists) exhibit the potency of opioid pain killers without their negative side effects, such as physical addiction, physical dependence, narcotic addiction, and like conditions. See P. W. Schiller et al., J. Med. Chem., 42, 3520 (1999).

As one example of the value of subtype-selective opioid receptor agents, recent evidence suggests that δ-selective opioids are potentially useful as analgesics devoid of the numerous side effects (e.g., respiratory depression, physical dependence and gastrointestinal effects) associated with narcotics such as morphine (E. J. Bilsky et al., J. Pharmacol. Exp. Ther., 273, 359 (1995)). Moreover, selective antagonists of δ receptors have been shown to modulate the development of tolerance and dependence to μ agonists such as morphine (E. E. Abdelhamid et al., J. Pharmacol. Exp. Ther., 258, 299 (1991)), to modulate the behavioral effects of drugs of abuse such as cocaine (L. D. Reid et al., Life Sci., 52, PL67 (1993)), and to elicit favorable immunomodulatory effects (R. V. House et al., Neurosci. Lett., 198, 119 (1995)). The δ-selective opioids thus represent extremely attractive candidates for a broad range of novel pharmaceutical applications including powerful yet safe analgesics, immunomodulatory agents for treating immune disorders, and new treatments for drug addiction.

Therefore, a need exists for non-opioid compounds which possess high binding affinity and high selectivity for delta (δ), kappa (κ), and mu (μ) opioid receptors. Such compounds would be useful for treating pain as well as other opioid-related conditions.

SUMMARY OF THE INVENTION

This need is met by the present invention, which relates to a compound of Formula I:

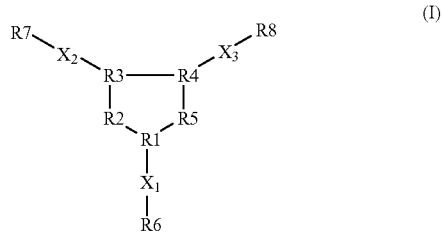

wherein $R_1$-$R_5$ define cyclopentane, cyclopentene, cyclopentadiene, or a five-membered heteroaromatic ring comprising from 1 to 3 heteroatoms and 2 to 4 carbon atoms, wherein $R_2$ and $R_5$ are selected from the group consisting of O, N, C=O, $NR_a$, S, and CH; and $R_1$, $R_3$, and $R_4$ are N or C;

$X_1$, $X_2$, and $X_3$ are independently a bond or a saturated or unsaturated alkylene group;

one of $R_6$, $R_7$, and $R_8$ is H, $(C_{1-7})$alkyl, $(C_{3-12})$cycloalkyl, aryl, Het, or a group that includes one or more basic atoms;

two of $R_6$, $R_7$, and $R_8$ are phenyl rings meta- or para-substituted with from one to three substituents each selected independently from aryl, halo, $OR_a$, trifluoromethoxy, trifluoromethyl, $NO_2$, $NR_aR_b$, cyano, $CONR_aR_b$, $CO_2R_a$, $SO_mR_a$, $S(O)_mNR_aR_b$, P(=O)($OR_a$)($R_a$), $(C_{1-7})$alkyl, $(C_{2-6})$alkenyl, $(C_{2-6})$alkynyl, $(C_{2-7})$alkanoyl, $(C_{2-7})$alkanoyloxy, $(C_{3-12})$cycloalkyl, $(C_{1-7})$acyl, Het, a naphthyl group having a structure selected from

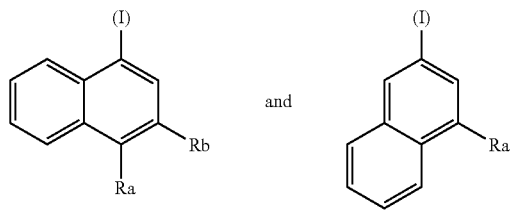

or fused-ring structure selected from

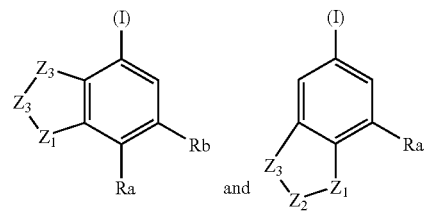

wherein (C$_{1-7}$)alkyl or (C$_{3-12}$)cycloalkyl are each independently optionally substituted with from 1 to 5 aryl, Het, OR$_a$, halo, NO$_2$, NR$_a$R$_b$, cyano, CONR$_a$R$_b$, CO$_2$R$_a$, SO$_m$R$_a$, S(O)$_m$NR$_a$R$_b$, or P(=O)(OR$_a$)(R$_a$);

wherein R$_a$ and R$_b$ are each independently H, (C$_{1-7}$)alkyl, (C$_{3-12}$)cycloalkyl, (C$_{2-7}$)alkanoyl, (C$_{2-7}$)alkanoyloxy, or aryl, or R$_a$ and R$_b$ together with a nitrogen to which they are attached form a Het;

Z$_1$, Z$_2$, and Z$_3$ are independently selected from O, N, C=O, NR$_a$, S, and CH;

m is 0, 1, or 2;

n is 0, 1, 2, 3, or 4;

wherein when Formula I is:

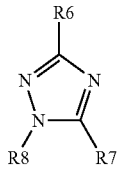

one of R$_6$, R$_7$, and R$_8$ is (C$_{1-7}$)alkyl or a group that includes one or more basic atoms;

or a derivative of said compound selected from N-oxide derivatives, prodrug derivatives, protected derivatives, isomers, and mixtures of isomers of said compound; or a pharmaceutically acceptable salt or solvate of said compound or said derivative.

Another aspect of the invention is a compound of Formula II:

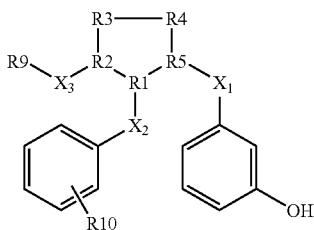

wherein

R$_1$-R$_5$ define cyclopentane, cyclopentene, cyclopentadiene, or a five-membered heteroaromatic ring containing from 1 to 3 heteroatoms and 2 to 4 carbon atoms, wherein R$_3$ and R$_4$ are selected from the group consisting of O, N, C=O, NR$_a$, CH and S; and R$_1$, R$_2$, and R$_5$ are C or N;

X$_1$, X$_2$, and X$_3$ are independently a bond or a saturated or unsaturated alkylene group;

R$_9$ is H, (C$_{1-7}$)alkyl, (C$_{3-12}$)cycloalkyl, aryl, Het, or a group that includes one or more basic atoms;

R$_{10}$ is meta- or para-substituted with from one to three substituents each selected independently from OR$_a$, aryl, halo, trifluoromethoxy, trifluoromethyl, NO$_2$, NR$_a$R$_b$, cyano, CONR$_a$R$_b$, CO$_2$R$_a$, SO$_m$R$_a$, S(O)$_m$NR$_a$R$_b$, P(=O)(OR$_a$)(R$_a$), (C$_{1-7}$)alkyl, (C$_{2-6}$)alkenyl, (C$_{2-6}$)alkynyl, (C$_{2-7}$)alkanoyl, (C$_{2-7}$)alkanoyloxy, (C$_{3-12}$)cycloalkyl, (C$_{1-7}$)acyl, Het, a naphthyl group having a structure selected from

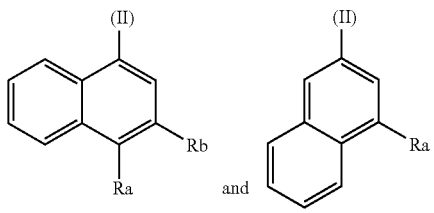

or a fused-ring structure selected from

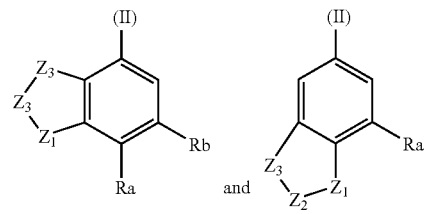

wherein (C$_{1-7}$)alkyl or (C$_{3-12}$)cycloalkyl are each independently optionally substituted with from 1 to 5 aryl, Het, OR$_a$, halo, NO$_2$, NR$_a$R$_b$, cyano, CONR$_a$R$_b$, CO$_2$R$_a$, SO$_m$R$_a$, S(O)$_m$NR$_a$R$_b$, or P(=O)(OR$_a$)(R$_a$);

R$_a$ and R$_b$ are each independently H, (C$_{1-7}$)alkyl, (C$_{3-12}$)cycloalkyl, (C$_{2-7}$)alkanoyl, (C$_{2-7}$)alkanoyloxy, or aryl, or R$_a$ and R$_b$ together with a nitrogen to which they are attached form a Het;

Z$_1$, Z$_2$, and Z$_3$ are independently selected from the group consisting of O, N, C=O, NR$_a$, S, and CH;

m is 0, 1, or 2;

n is 0, 1, 2, 3, or 4;

wherein when formula II is:

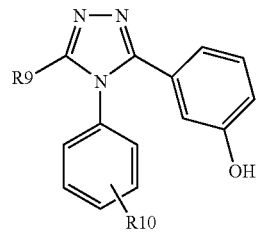

R$_9$ is (C$_{1-7}$)alkyl, (C$_{3-12}$)cycloalkyl, aryl, Het, or a group that includes one or more basic atoms;

and R$_{10}$ is meta- or para-substituted with from one to three substituents each selected independently from aryl, halo, trifluoromethoxy, trifluoromethyl, NO$_2$, NR$_a$R$_b$, cyano, CONR$_a$R$_b$, CO$_2$R$_a$, SO$_m$R$_a$, S(O)$_m$NR$_a$R$_b$, P(=O)(OR$_a$)(R$_a$), (C$_{1-7}$)alkyl, (C$_{2-6}$)alkenyl, (C$_{2-6}$)alkynyl, (C$_{2-7}$)alkanoyl, (C$_{2-7}$)alkanoyloxy, (C$_{3-12}$)cycloalkyl, (C$_{1-7}$)acyl, Het, a naphthyl group having a structure selected from

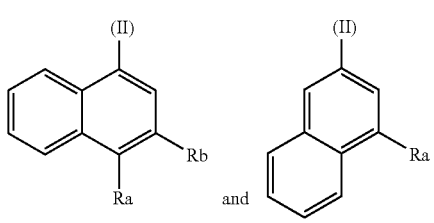

or a fused-ring structure selected from

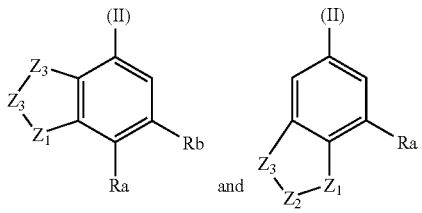

or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

Another embodiment of the present invention is a compound of Formula III(a) or III(b):

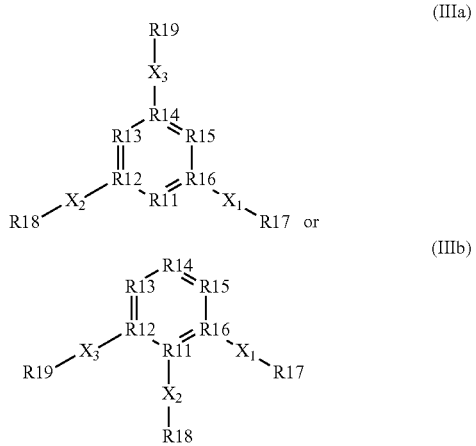

wherein $R_{11-16}$ define phenyl or a six-membered heteroaromatic ring comprising from 1 to 3 heteroatoms and 3 to 5 carbon atoms, wherein $R_{11}$, $R_{13}$, and $R_{15}$ of formula IIIa and $R_{13}$, $R_{14}$, and $R_{15}$ of formula IIIb are selected from the group consisting of O, N, C=O, $NR_a$, S, and CH; and $R_{12}$, $R_{14}$, and $R_{16}$ of formula IIIa and $R_{11}$, $R_{12}$ and $R_{16}$ of formula IIIb are N or C;

$X_1$, $X_2$, and $X_3$ are independently a bond or a saturated or unsaturated alkylene group;

one of $R_{17}$, $R_{18}$, and $R_{19}$ is H, $(C_{1-7})$alkyl, $(C_{3-12})$cycloalkyl, aryl, Het, or a group that includes one or more basic atoms;

two of $R_{17}$, $R_{18}$, and $R_{19}$ are meta- or para-substituted with from one to three substituents each selected $OR_a$, aryl, halo, trifluoromethoxy, trifluoromethyl, $NO_2$, $NR_aR_b$, cyano, $CONR_aR_b$, $CO_2R_a$, $SO_mR_a$, $S(O)_mNR_aR_b$, $P(=O)(OR_a)(R_a)$, $(C_{1-7})$alkyl, $(C_{2-6})$alkenyl, $(C_{2-6})$alkynyl, $(C_{2-7})$alkanoyl, $(C_{2-7})$alkanoyloxy, $(C_{3-12})$cycloalkyl, $(C_{1-7})$acyl, Het, a naphthyl group having a structure selected from

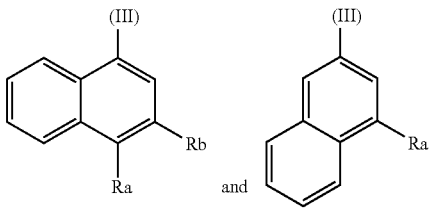

or a fused-ring structure selected from

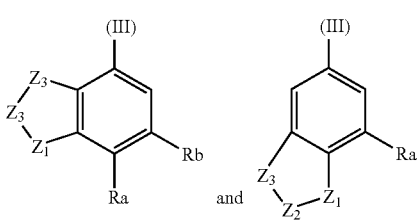

wherein $(C_{1-7})$alkyl or $(C_{3-12})$cycloalkyl are each independently optionally substituted with from 1 to 5 aryl, Het, $OR_a$, halo, $NO_2$, $NR_aR_b$, cyano, $CONR_aR_b$, $CO_2R_a$, $SO_mR_a$, $S(O)_mNR_aR_b$, or $P(=O)(OR_a)(R_a)$;

$R_a$ and $R_b$ are each independently H, $(C_{1-7})$alkyl, $(C_{3-12})$cycloalkyl, $(C_{2-7})$alkanoyl, $(C_{2-7})$alkanoyloxy, or aryl, or $R_a$ and $R_b$ together with a nitrogen to which they are attached form a Het;

$Z_1$, $Z_2$, and $Z_3$ are independently selected from the group consisting of O, N, C=O, $NR_a$, S, and CH;

m is 0, 1, or 2;

n is 0, 1, 2, 3, or 4;

or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

Another embodiment of the present invention is a compound comprising a structure selected from formulas IVa-IVd:

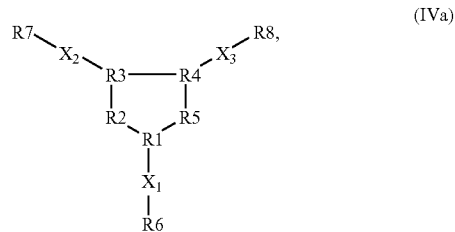

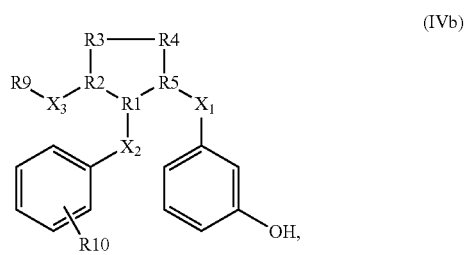

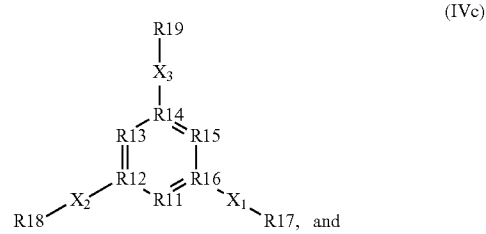

-continued (IVd)

wherein $R_1$-$R_5$ define cyclopentane, cyclopentene, cyclopentadiene, or a five-membered heteroaromatic ring comprising from 1 to 3 heteroatoms and 2 to 4 carbon atoms, wherein in formula IVa $R_2$ and $R_5$ are selected from the group consisting of O, N, C=O, $NR_a$, S, and CH; and $R_1$, $R_3$, and $R_4$ are N or C; in formula IVb $R_3$ and $R_4$ are selected from the group consisting of O, N, C=O, $NR_a$, CH and S; and $R_1$, $R_2$, and $R_5$ are C or N;

$R_{11-16}$ define phenyl or a six-membered heteroaromatic ring comprising from 1 to 3 heteroatoms and 3 to 5 carbon atoms, wherein $R_1$, $R_{13}$, and $R_{15}$ of formula IVc and $R_{13}$, $R_{14}$, and $R_{15}$ of formula IVd are selected from the group consisting of O, N, C=O, $NR_a$, S, and CH; and $R_{12}$, $R_{14}$, and $R_{16}$ of formula IVc and $R_{11}$, $R_{12}$ and $R_{16}$ of formula IVd are N or C;

$X_1$, $X_2$, and $X_3$ are independently a bond or a saturated or unsaturated alkylene group;

$R_9$ or one of $R_6$, $R_7$, and $R_8$ or one of $R_{17}$, $R_{18}$, or $R_{19}$ is H, $(C_{1-7})$alkyl, $(C_{3-12})$cycloalkyl, aryl, Het, or a group that includes one or more basic atoms;

$R_{10}$ or two of $R_6$, $R_7$, and $R_8$ or two of $R_{17}$, $R_{18}$, or $R_{19}$ are phenyl rings meta- or para-substituted with from one to three substituents each selected independently from the group consisting of aryl, halo, $OR_a$, trifluoromethoxy, trifluoromethyl, $NO_2$, $NR_aR_b$, cyano, $CONR_aR_b$, $CO_2R_a$, $SO_mR_a$, $S(O)_mNR_aR_b$, $P(=O)(OR_a)(R_a)$, $(C_{1-7})$alkyl, $(C_{2-6})$alkenyl, $(C_{2-6})$alkynyl, $(C_{2-7})$alkanoyl, $(C_{2-7})$alkanoyloxy, $(C_{3-12})$cycloalkyl, $(C_{1-7})$acyl, Het, a naphthyl group having a structure selected from (IV)   (IV)

and or a fused-ring structure selected from (IV)   (IV)

and wherein $(C_{1-7})$alkyl or $(C_{3-12})$cycloalkyl are each independently optionally substituted with from 1 to 5 aryl, Het, $OR_a$, halo, $NO_2$, $NR_aR_b$, cyano, $CONR_aR_b$, $CO_2R_a$, $SO_mR_a$, $S(O)_mNR_aR_b$, or $P(=O)(OR_a)(R_a)$;

$R_a$ and $R_b$ are each independently H, $(C_{1-7})$alkyl, $(C_{3-12})$cycloalkyl, $(C_{2-7})$alkanoyl, $(C_{2-7})$alkanoyloxy, or aryl, or $R_a$ and $R_b$ together with a nitrogen to which they are attached form a Het;

$Z_1$, $Z_2$, and $Z_3$ are independently selected from the group consisting of O, N, C=O, $NR_a$, S, and CH;

m is 0, 1, or 2;

n is 0, 1, 2, 3, or 4; and at least one substituent of a ring structure carries a fixed charge sustainable under physiological conditions;

or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

Another aspect of the invention is a pharmaceutical composition comprising a pharmaceutically effective amount of a compound of the present invention and a pharmaceutically acceptable carrier.

Also provided is a method for preventing, diagnosing, or treating a condition mediated by an opioid receptor comprising administering an effective amount of a compound of the present invention to a patient in need thereof.

BRIEF DESCRIPTION OF THE DRAWINGS

FIG. 1 is a representative competition curve of DOP108 at the δ opioid receptor; and FIG. 2 is a graph showing the effect of compounds of Formula I on activity of delta receptors.

DETAILED DESCRIPTION OF THE INVENTION

The present invention relates to opioid receptor-mediating compounds. Also presented are methods for treating a condition mediated by an opioid receptor.

As used above, and throughout the description of the invention, the following terms, unless otherwise indicated, shall be understood to have the following meanings:

"Patient" means a mammal including a human.

"Effective amount" means an amount of compound of the present invention effective for treating opioid receptor related diseases or conditions, and thus producing the desired therapeutic effect.

"Treat" or "treatment" or "treating" mean to lessen, eliminate, inhibit, improve, alter, or prevent a disease or condition, for example by administration of compound of the present invention.

"Pain" refers to, for example, a localized or generalized physical suffering associated with bodily disorder, such as a disease or an injury, and can include a basic bodily sensation induced by a noxious stimulus, received by naked nerve endings, characterized by physical discomfort such as pricking, throbbing, or aching, and typically leads to evasive action. A specific example is neuropathic pain which is a chronic condition associated with diabetes, chronic inflammation, cancer, and herpes virus infection.

"Analgesia" or "pain relief" includes, for example, inducing or providing insensitivity to pain, and preferably without loss of consciousness.

"Diseases or conditions where an opioid receptors are implicated" and "opioid receptor related disease or conditions" include, inflammation (e.g. inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, swelling occurring after injury, myocardial ischemia, allergic rhinitis, respiratory distress syndrome, endotoxin shock syndrome, atherosclerosis), pain, headache, fever, arthritis (including rheumatoid arthritis, spondyloarthopathies, gouty arthritis, osteoarthritis, systemic lupus erythematosus, and juvenile arthritis), asthma, bronchitis, menstrual cramps, tendinitis, bursitis, skin related conditions (e.g. psoriasis, eczema, burns and dermatitis), gastrointestinal conditions (e.g. inflammatory bowel disease, Crohn's disease, gastritis, irritable bowel syndrome, and ulcerative colitis), cancer (e.g. colorectal cancer), ophthalmic diseases (e.g. retinitis, retinopathies, conjunctivitis, uveitis, ocular photophobia, and acute injury to the eye tissue), pulmonary inflammation (such as that associated with viral infections and cystic fibrosis), central nervous system disorders (such as cortical dementias including Alzheimer's disease), and central nervous system damage (e.g. resulting from stroke, ischemia, or trauma). Compounds of the invention may also be useful for modifying the effects of other biologically active compounds (for example for treating narcotic addiction), and for treating diseases or conditions other than ones associated with receptors, for example, blocking, inhibiting, or promoting, metabolic pathways or enzyme function, and selectively interacting with genetic material.

"Alkyl" means aliphatic hydrocarbon group which may be branched or straight-chained having about 1 to about 10 carbon atoms. Preferred alkyl is "lower alkyl" having about 1 to about 3 carbon atoms; more preferred is methyl. Branched means that one or more lower alkyl groups such as methyl, ethyl, or propyl are attached to a linear alkyl chain. The alkyl group is also optionally substituted by alkoxy, halo, carboxy, hydroxy or $R_eR_fN$— (wherein $R_e$ and $R_f$ are independently hydrogen or alkyl, or $R_e$ and $R_f$ taken together with the nitrogen atom to which $R_e$ and $R_f$ are attached form azaheterocyclyl); and preferably optionally substituted by fluoro. Examples of alkyl include methyl, fluoromethyl, difluoromethyl, trifluoromethyl, ethyl, n-propyl, isopropyl, butyl, sec-butyl, t-butyl, amyl and hexyl.

"Cycloalkyl" means a non-aromatic monocyclic ring system of about 3 to about 7 carbon atoms. Preferred monocyclic cycloalkyl rings include cyclopentyl, cyclohexyl, and cycloheptyl; more preferred are cyclohexyl and cyclopentyl.

"Aryl" means aromatic carbocyclic radical containing about 6 to about 10 carbon atoms. Exemplary aryl include phenyl or naphthyl, or phenyl or naphthyl substituted with one or more aryl group substituents which may be the same or different, where "aryl group substituent" includes hydrogen, hydroxy, halo, alkyl, alkoxy, carboxy, alkoxycarbonyl or $Y_1Y_2NCO$—, wherein $Y_1$ and $Y_2$ are independently hydrogen or alkyl.

"Het" is a four- (4), five- (5), six- (6), or seven- (7) membered saturated or unsaturated heterocyclic ring having 1, 2, 3, or 4 heteroatoms selected from the group consisting of oxy, thio, sulfinyl, sulfonyl, and nitrogen, which ring is optionally fused to a benzene ring. Het includes "heteroaryl," which encompasses about a 5- to about a 10-membered aromatic monocyclic or bicyclic hydrocarbon ring system in which one to three of the atoms in a monocyclic ring system, and one to four of the atoms in a bicyclic ring system, is/are elements(s) other than carbon, for example nitrogen, oxygen or sulfur. The "heteroaryl" may also be substituted by one or more of the above-mentioned "aryl group substituents". Exemplary heteroaryl groups include substituted pyrazinyl, furanyl, thienyl, pyridyl, pyrimidinyl, isoxazolyl, isothiazolyl, oxazolyl, thiazoly, pyrazolyl, furazanyl, pyrrolyl, imidazo[2,1-b]thiaz-olyl, benzofurzanyl, indolyl, azaindolyl, benzimidazolyl, benzothienyl, quinolinyl, imidazolyl and isoquinolinyl.

"Acyl" means an H—CO— or alkyl-CO— group in which the alkyl group is as previously described. Preferred acyls contain a lower alkyl. Exemplary acyl groups include formyl, acetyl, propanoyl, 2-methylpropanoyl, butanoyl and caproyl.

"Alkoxy" means an alkyl-O— group in which the alkyl group is as previously described. Preferred alkoxy is "lower alkoxy" having about 1 to about 3 carbon atoms; more preferred is methoxy. The alkoxy may be optionally substituted by one or more alkoxy, carboxy, alkoxycarbonyl, carboxyaryl or $R_eR_fN$— (wherein $R_e$ and $R_f$ are as defined above). Exemplary alkoxy groups include methoxy, ethoxy, n-propoxy, i-propoxy, n-butoxy, heptoxy, 2-(morpholin-4-yl)ethoxy and 2-(ethoxy)ethoxy.

"Aryloxy" means aryl-O— group in which the aryl group is as previously described.

"Acyloxy" means and acyl-O— group in which the acyl group is as previously described.

"Carboxy" means a HO(O)C— (carboxylic acid) group.

"$R_eR_fN$—" means a substituted or unsubstituted amino group, wherein $R_e$ and $R_f$ are as previously described. Exemplary groups include amino ($H_2N$—), methylamino, ethylmethylamino, dimethylamino and diethylamino.

"$R_eR_fNCO$—" means a substituted or unsubstituted carbomoyl group, wherein $R_e$ and $R_f$ are as previously described. Exemplary groups are carbamoyl ($H_2NCO$—) are dimethylaminocarbamoyl ($Me_2NCO$—).

"$AcylR_eN$—" means an acylamino group wherein $R_e$ and acyl are as defined herein.

"Halo" means fluoro, chloro, bromo, or iodo. Preferred are fluoro, chloro or bromo, and more preferred are fluoro or chloro.

"Prodrug" means a form of the compound of formula I suitable for administration to a patient without undue toxicity, irritation, allergic response, and the like, and effective for their intended use. A prodrug is transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, et., Bioreversible Carriers in Drug Design, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are $H_2O$.

"Substituent of a ring structure" means any atom or group of atoms bonded to a ring in a molecule.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase). It is also well known in the art and, for example, as illustrated hereinbelow how to determine opioid receptor activity, for example, delta, mu, or kappa, or related receptor activity using the standard tests described herein, or using other similar tests. In particular, it is understood that compounds of formulas I-IV can contain chiral centers, for example, in any of the $R_a$-$R_b$, $R_6$-$R_{10}$, and $R_{17}$-$R_{19}$ substituents.

One embodiment of the present invention is a compound of formula I, wherein $R_1$-$R_5$ is a five-membered heteroaromatic ring selected from 1,3-dioxolane; pyrazolidine; imidazoline; 2-pyrazoline with one chiral center; 2-imidazoline; pyrazole (1,2-diazole); 1H-imidazole; 1,2,3-triazole; 1,2,4-triazole; 2-thiazole; 3H-1,2-dithiole; 2H-1,3-dithiole; 3H-1,2-oxathiole; isoxazole (1,2-oxazole); oxazole(1,3-oxazole); thioazole (1,3-thiazole); isothiazole(1,2-thiazole); 1,2,3-oxadiazole; 1,2,4-oxadiazole; 1,2,5-oxadiazole(furazan); 1,3,4-oxatriazole; 1,2,3,4-oxatriazole; 1,2,3,5-oxatriazole; 3H-1,2,3-dioxazole; and 1,2,4-dioxazole.

Another embodiment of the invention is a compound of formula I, wherein $R_1$-$R_5$ define a 1,2,4-triazole and $R_6$, $R_7$, and $R_8$ are independently selected from $CH_2N(CH_3)_2$, m-tert-butyl phenyl, p-tert-butyl phenyl, 3,4-dimethyl phenyl, phenol, and methoxy benzyl.

Yet another embodiment of the present invention is a compound of Formula II:

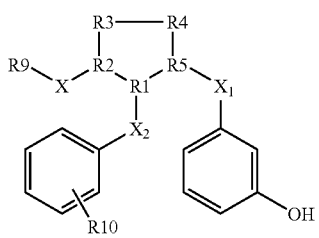

$R_1$-$R_5$ define cyclopentane, cyclopentene, cyclopentadiene, or a five-membered heteroaromatic ring containing from 1 to 3 heteroatoms and 2 to 4 carbon atoms, wherein $R_3$ and $R_4$ are selected from the group consisting of O, N, C=O, $NR_a$, CH and S; and $R_1$, $R_2$, and $R_5$ are C or N;

$X_1$, $X_2$, and $X_3$ are independently a bond or a saturated or unsaturated alkylene group;

$R_9$ is H, $(C_{1-7})$alkyl, $(C_{3-12})$cycloalkyl, aryl, Het, or a group that includes one or more basic atoms;

$R_{10}$ is meta- or para-substituted with from one to three substituents each selected independently from the group consisting of $OR_a$, aryl, halo, trifluoromethoxy, trifluoromethyl, $NO_2$, $NR_aR_b$, cyano, $CONR_aR_b$, $CO_2R_a$, $SO_mR_a$, $S(O)_mNR_aR_b$, $P(=O)(OR_a)(R_a)$, $(C_{1-7})$alkyl, $(C_{2-6})$alkenyl, $(C_{2-6})$alkynyl, $(C_{2-7})$alkanoyl, $(C_{2-7})$alkanoyloxy, $(C_{3-12})$cycloalkyl, $(C_{1-7})$acyl, Het, a naphthyl group having a structure selected from

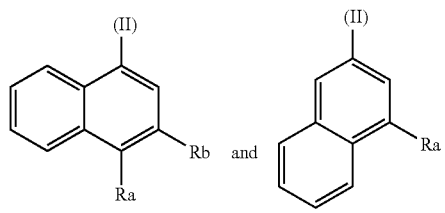

or a fused-ring structure selected from

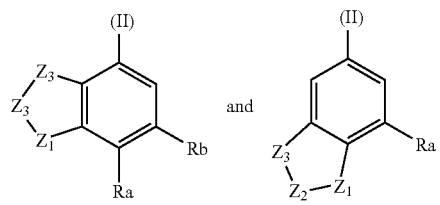

wherein $(C_{1-7})$alkyl or $(C_{3-12})$cycloalkyl are each independently optionally substituted with from 1 to 5 aryl, Het, $OR_a$, halo, $NO_2$, $NR_aR_b$, cyano, $CONR_aR_b$, $CO_2R_a$, $SO_mR_a$, $S(O)_mNR_aR_b$, or $P(=O)(OR_a)(R_a)$;

$R_a$ and $R_b$ are each independently H, $(C_{1-7})$alkyl, $(C_{3-12})$cycloalkyl, $(C_{2-7})$alkanoyl, $(C_{2-7})$alkanoyloxy, or aryl, or $R_a$ and $R_b$ together with a nitrogen to which they are attached form a Het;

$Z_1$, $Z_2$, and $Z_3$ are independently selected from the group consisting of O, N, C=O, $NR_a$, S, and CH;

m is 0, 1, or 2;

n is 0, 1, 2, 3, or 4;

wherein when formula II is:

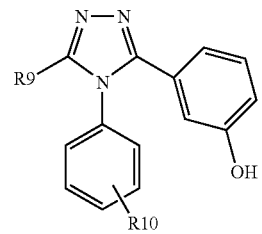

$R_9$ is $(C_{1-7})$alkyl, $(C_{3-12})$cycloalkyl, aryl, Het, or a group that includes one or more basic atoms;

and $R_{10}$ is meta- or para-substituted with from one to three substituents each selected independently from the group consisting of aryl, halo, trifluoromethoxy, trifluoromethyl, $NO_2$, $NR_aR_b$, cyano, $CONR_aR_b$, $CO_2R_a$, $SO_mR_a$, $S(O)_mNR_aR_b$, $P(=O)(OR_a)(R_a)$, $(C_{1-7})$alkyl, $(C_{2-6})$alkenyl, $(C_{2-6})$alkynyl, $(C_{2-7})$alkanoyl, $(C_{2-7})$alkanoyloxy, $(C_{3-12})$cycloalkyl, $(C_{1-7})$acyl, Het, a naphthyl group having a structure selected from

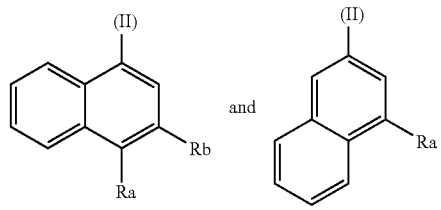

or a fused-ring structure selected from

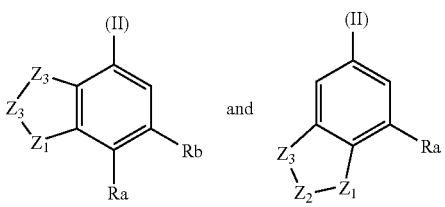

or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

Another embodiment of the present invention is a compound of formula I or II, wherein the compound has 0 to 2 chiral centers.

Another embodiment of the present invention is a compound of formula I, wherein one of $R_6$, $R_7$, and $R_8$ is hydrogen, a substituted amino alkyl, or a substituted primary, secondary, or tertiary amine.

Another embodiment of the present invention is a compound of formula II, wherein $R_9$ is $N(CH_3)_2$ and $R_{10}$ is selected from the group consisting of m-tert-butyl, p-tert-butyl, and hydroxyl.

Another embodiment of the present invention is a compound of formula II, wherein $R_9$ is hydrogen, a substituted amino alkyl, or a substituted primary, secondary, or tertiary amine.

Another embodiment of the present invention includes the following compounds:

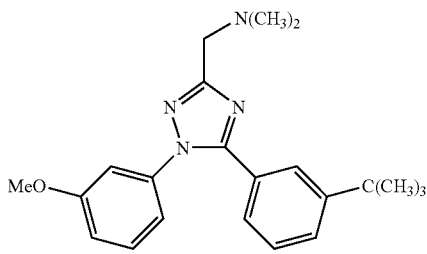
(DOP 105)

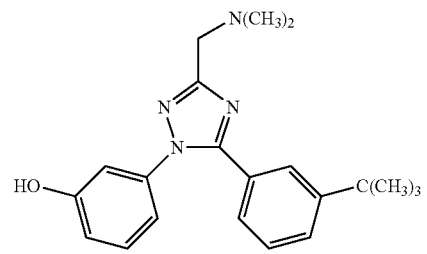
(DOP 106)

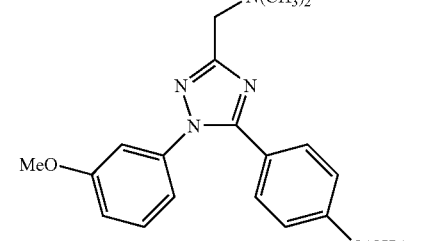
(DOP 107)

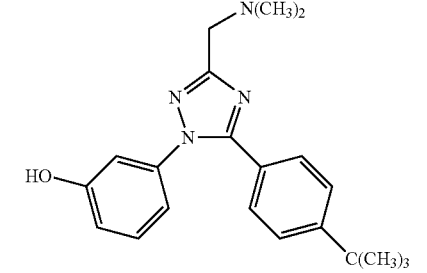
(DOP 108)

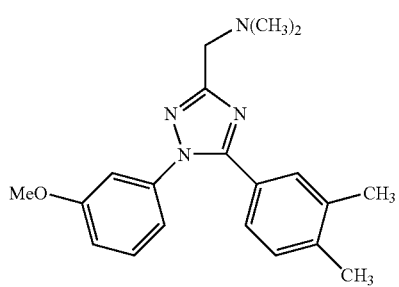
(DOP 109)

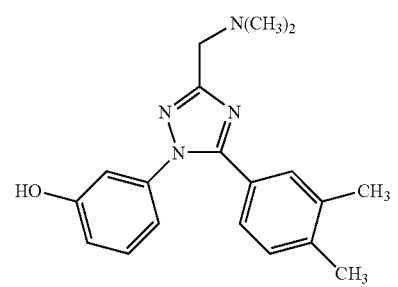
(DOP 110)

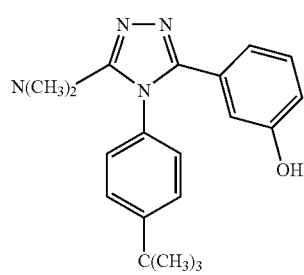
(DST8S)

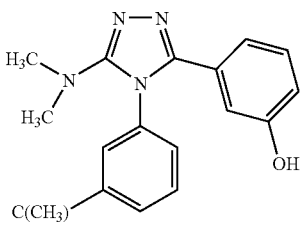
(DST10S)

Another embodiment of the present invention is a compound having a structure selected from formulas IVa-IVd:

(IVa)

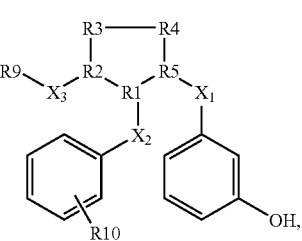
(IVb)

-continued

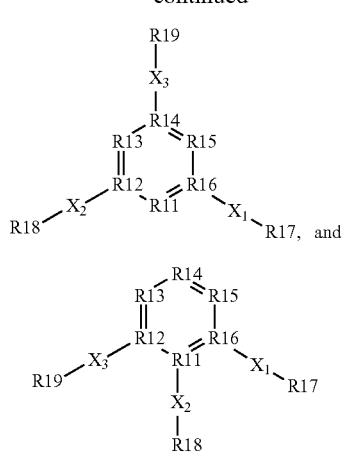

wherein

R₁-R₅ define cyclopentane, cyclopentene, cyclopentadiene, or a five-membered heteroaromatic ring comprising from 1 to 3 heteroatoms and 2 to 4 carbon atoms, wherein in formula IVa R₂ and R₅ are selected from the group consisting of O, N, C=O, NR$_a$, S, and CH; and R₁, R₃, and R₄ are N or C; in formula IVb R₃ and R₄ are selected from the group consisting of O, N, C=O, NR$_a$, CH and S; and R₁, R₂, and R₅ are C or N;

R₁₁₋₁₆ define phenyl or a six-membered heteroaromatic ring comprising from 1 to 3 heteroatoms and 3 to 5 carbon atoms, wherein R₁₁, R₁₃, and R₁₅ of formula IVc and R₁₃, R₁₄, and R₁₅ of formula IVd are selected from the group consisting of O, N, C=O, NR$_a$, S, and CH; and R₁₂, R₁₄, and R₁₆ of formula IVc and R₁₁, R₁₂ and R₁₆ of formula IVd are N or C;

X₁, X₂, and X₃ are independently a bond or a saturated or unsaturated alkylene group;

R₉ or one of R₆, R₇, and R₈ or one of R₁₇, R₁₈, or R₁₉ is H, (C₁₋₇)alkyl, (C₃₋₁₂)cycloalkyl, aryl, Het, or a group that includes one or more basic atoms;

R₁₀ or two of R₆, R₇, and R₈ or two of R₁₇, R₁₈, or R₁₉ are phenyl rings meta- or para-substituted with from one to three substituents each selected independently from the group consisting of aryl, halo, OR$_a$, trifluoromethoxy, trifluoromethyl, NO₂, NR$_a$R$_b$, cyano, CONR$_a$R$_b$, CO₂R$_a$, SO$_m$R$_a$, S(O)$_m$NR$_a$R$_b$, P(=O)(OR$_a$)(R$_a$), (C₁₋₇)alkyl, (C₂₋₆)alkenyl, (C₂₋₆)alkynyl, (C₂₋₇)alkanoyl, (C₂₋₇)alkanoyloxy, (C₃₋₁₂)cycloalkyl, (C₁₋₇)acyl, Het, a naphthyl group having a structure selected from

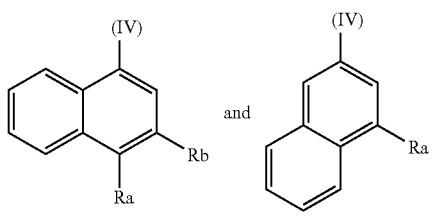

or a fused-ring structure selected from

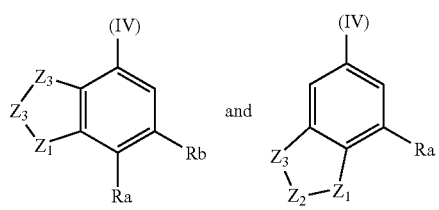

wherein (C₁₋₇)alkyl or (C₃₋₁₂)cycloalkyl are each independently optionally substituted with from 1 to 5 aryl, Het, OR$_a$, halo, NO₂, NR$_a$R$_b$, cyano, CONR$_a$R$_b$, CO₂R$_a$, SO$_m$R$_a$, S(O)$_m$NR$_a$R$_b$, or P(=O)(OR$_a$)(R$_a$);

R$_a$ and R$_b$ are each independently H, (C₁₋₇)alkyl, (C₃₋₁₂)cycloalkyl, (C₂₋₇)alkanoyl, (C₂₋₇)alkanoyloxy, or aryl, or R$_a$ and R$_b$ together with a nitrogen to which they are attached form a Het;

Z₁, Z₂, and Z₃ are independently selected from the group consisting of O, N, C=O, NR$_a$, S, and CH;

m is 0, 1, or 2;

n is 0, 1, 2, 3, or 4; and at least one substituent of a ring structure carries a fixed charge sustainable under physiological conditions;

or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

Another embodiment of the present invention includes the following compounds:

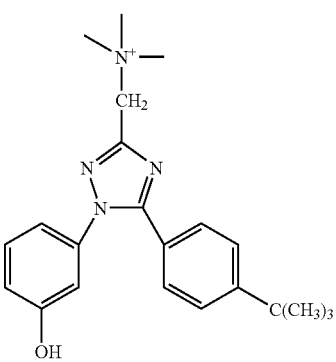

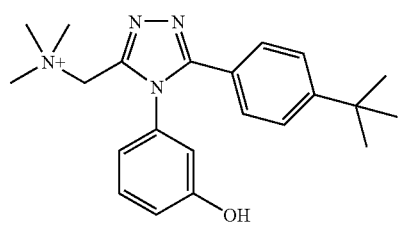

It is to be understood that this invention covers all appropriate combinations of the particular and preferred groupings referred to herein.

The compounds of this invention may be prepared by employing procedures known in the literature starting from known compounds or readily prepared intermediates. Exemplary general procedures follow.

Compounds of formula I can be prepared according to the following exemplary schemes, wherein the variables are as described above, excepting those variables which one skilled in the art would appreciate would be incongruent with the method described. It is noted that R$_c$ and R$_d$ in the following schemes designate the substituents of R₇ and R₈ respectively.

Scheme I.

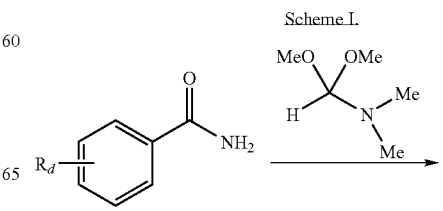

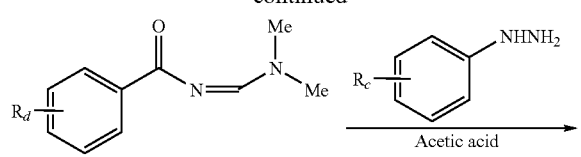
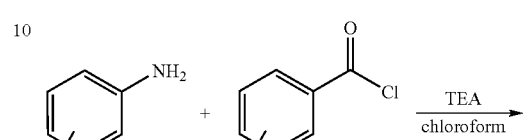
Compounds of formula II can be prepared according to the following exemplary schemes, wherein the variables are as described above, excepting those variables which one skilled in the art would appreciate would be incongruent with the method described.
Scheme II.
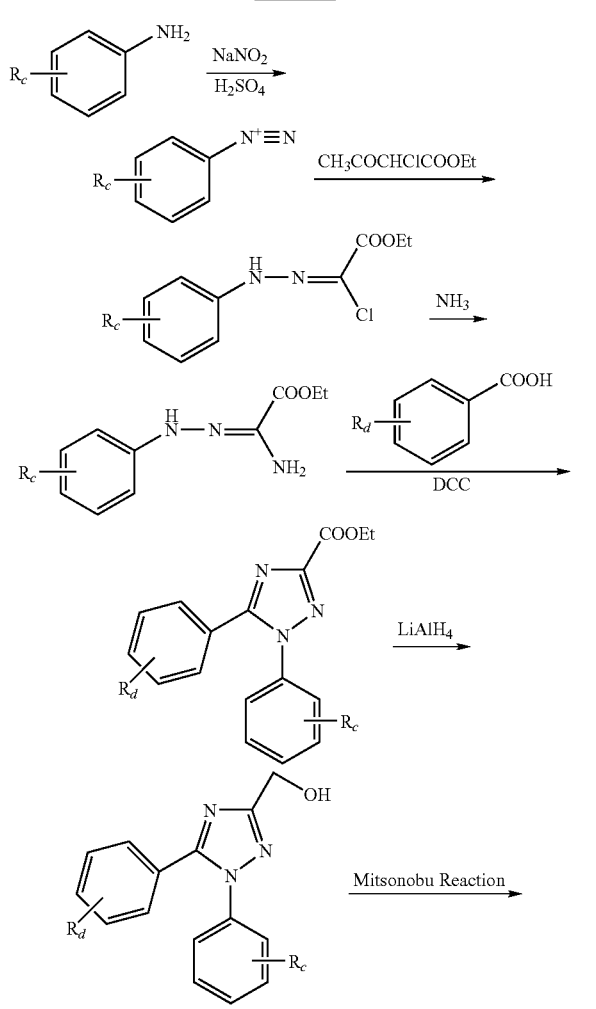
Scheme III.
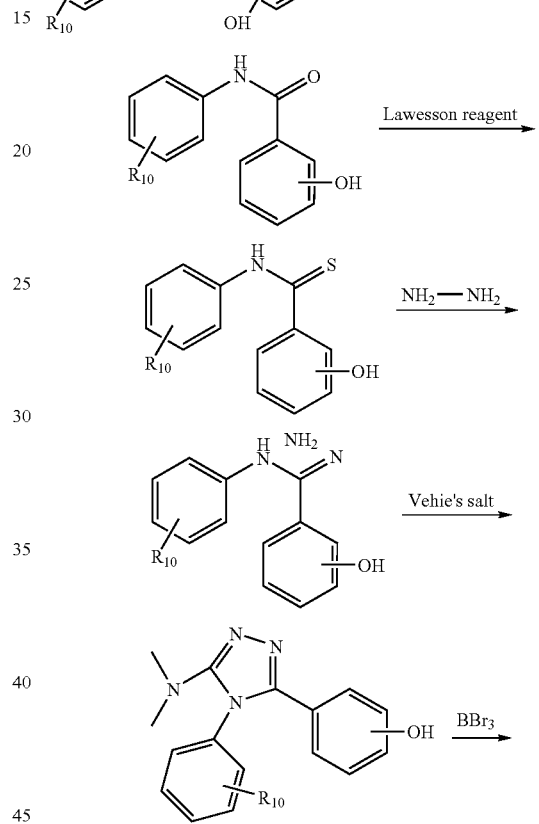
Scheme IV.
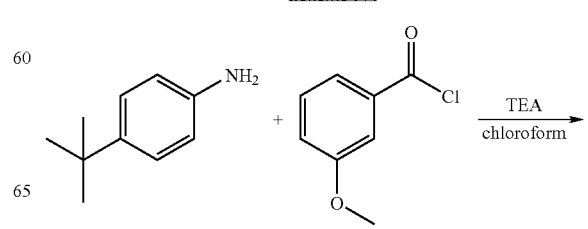

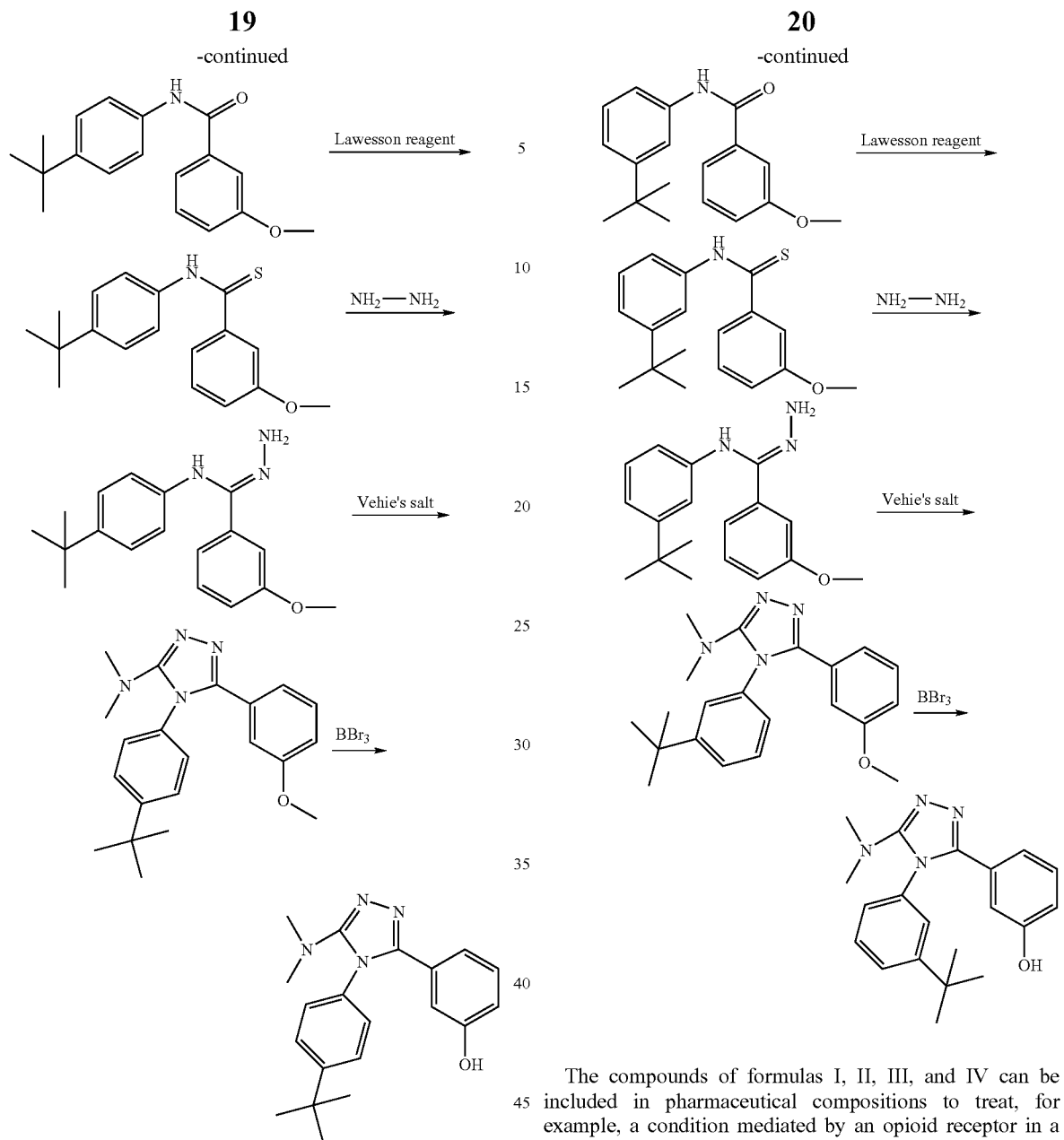

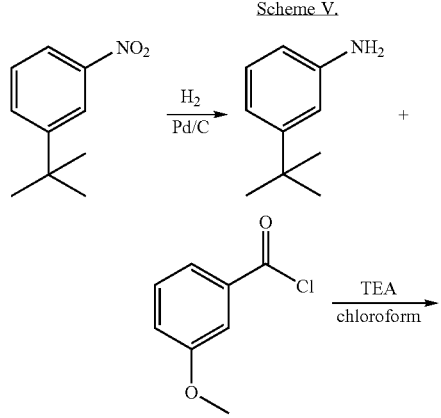

The compounds of formulas I, II, III, and IV can be included in pharmaceutical compositions to treat, for example, a condition mediated by an opioid receptor in a patient. Examples of targeted opioid receptors include delta (δ), mu (μ), and kappa (κ) opioid receptors. The compounds of the present invention can act as selective agonists or antagonists of these receptors. The compounds can also function as mixed agonist/antagonist opioid receptor agents, which exhibit the desired therapeutic effect of an opioid with a reduction in undesirable, unacceptable, or toxic side effects, such as physical addiction, physical dependence, narcotic addiction, and the like. Further, by converting at least one substituent of a ring in a compound of the present invention to a species having a fixed charge, such as a quaternary nitrogen atom or a carboxylate ion, the compounds of the present invention can be largely excluded from the brain and will exert primarily peripheral actions.

Conditions mediated by an opioid receptor include, but are not limited to, those disclosed in U.S. Publication No. 2003-0225072 A1, the contents of which are incorporated herein by reference in their entirety, inflammation (e.g. inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, swelling occurring after injury, myocardial ischemia, allergic rhinitis, respiratory distress syndrome, endotoxin shock syndrome, atherosclerosis), pain, headache, fever, depression, stress, anxiety, arthritis (including rheumatoid arthritis, spondyloarthopathies, gouty arthritis, osteoarthritis, systemic lupus erythematosus, and juvenile arthritis), asthma, bronchitis, cough, menstrual cramps, tendinitis, bursitis, skin related conditions (e.g. psoriasis, eczema, burns and dermatitis), gastrointestinal conditions (e.g. inflammatory bowel disease, Crohn's disease, gastritis, irritable bowel syndrome, and ulcerative colitis), cancer (e.g. colorectal cancer), ophthalmic diseases (e.g. retinitis, retinopathies, conjunctivitis, uveitis, ocular photophobia, and acute injury to the eye tissue), pulmonary inflammation (such as that associated with viral infections and cystic fibrosis), cardiovascular diseases (such as stroke), acute pulmonary edema, central nervous system disorders (such as cortical dementias including Alzheimer's disease), peripheral nervous system damage (such as peripheral neuropathy), central nervous system damage (e.g. resulting from stroke, ischemia, or trauma), and organ transplantation. The compounds can also provide cytoprotective effects.

Therefore, also provided is a pharmaceutical composition comprising a pharmaceutically effective amount of the compound of formula I, II, III, IV, or a combination thereof and a pharmaceutically acceptable carrier.

In one embodiment, the pharmaceutical composition further includes a µ-agonist. In another embodiment, the µ-agonist is morphine or fentanyl.

Also provided is a method for preventing, diagnosing, or treating a condition mediated by a peripheral opioid receptor, said method comprising administering an effective amount of the compound of formula I, II, III, IV, or a combination thereof to a patient in need thereof.

In practice, a composition containing a compound of formula I, II, III, or IV may be administered in any variety of suitable forms, for example, by inhalation, topically, parenterally, rectally, or orally. More specific routes of administration include intravenous, intramuscular, subcutaneous, intraocular, intrasynovial, colonical, peritoneal, transepithelial including transdermal, ophthalmic, sublingual, buccal, dermal, ocular, nasal inhalation via insufflation, and aerosol.

A composition containing a compound of formula I, II, III, or IV may be presented in forms permitting administration by the most suitable route. The invention also relates to administering compositions containing a compound of formula I, II, III, or IV which is suitable for use as a medicament in a patient. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of oral dosage forms, or injectable solutions, or suspensions.

The choice of vehicle and the compound of formula I, II, III, or IV in the vehicle are generally determined in accordance with the solubility and chemical properties of the product, the particular mode of administration and the provisions to be observed in pharmaceutical practice. When aqueous suspensions are used they may contain emulsifying agents or agents which facilitate suspension. Diluents such as sucrose, ethanol, polyols such as polyethylene glycol, propylene glycol and glycerol, and chloroform or mixtures thereof may also be used. In addition, the compound of formula I, II, III, or IV may be incorporated into sustained-release preparations and formulations.

For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The injectable forms must be fluid to the extent that it can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The solutions of the salts of the products according to the invention are especially useful for administration by intramuscular or subcutaneous injection. Solutions of the compound of formula I, II, III, or IV as a free base or pharmacologically acceptable salt can be prepared in water suitably mixed with a surfactant such as hydroxypropyl-cellulose. Dispersion can also be prepared in glycerol, liquid polyethylene glycols, and mixtures thereof and in oils. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation, microfiltration, and/or by various antibacterial and antifungal agents, for example, parabens, chlorobutanol, phenol, sorbic acid, thimerosal, and the like.

Sterile injectable solutions are prepared by incorporating the compound of formula I, II, III, or IV in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile-filtered solution thereof.

Topical administration, gels (water or alcohol based), creams or ointments containing the compound of formula I, II, III, or IV may be used. The compound of formula I, II, III, or IV may be also incorporated in a gel or matrix base for application in a patch, which would allow a controlled release of compound through transdermal barrier.

For administration by inhalation, the compound of formula I, II, III, or IV may be dissolved or suspended in a suitable carrier for use in a nebulizer or a suspension or solution aerosol, or may be absorbed or adsorbed onto a suitable solid carrier for use in a dry powder inhaler.

Compositions according to the invention may also be formulated in a manner which resists rapid clearance from the vascular (arterial or venous) wall by convection and/or diffusion, thereby increasing the residence time of the particles at the desired site of action. A periadventitial depot comprising a compound according to the invention may be used for sustained release. One such useful depot for administering a compound according to the invention may be a copolymer matrix, such as ethylene-vinyl acetate, or a polyvinyl alcohol gel surrounded by a Silastic shell. Alternatively, a compound according to the invention may be delivered locally from a silicone polymer implanted in the adventitia.

An alternative approach for minimizing washout of a compound according to the invention during percutaneous, transvascular delivery comprises the use of nondiffusible, drug-eluting microparticles. The microparticles may be comprised of a variety of synthetic polymers, such as polylactide for example, or natural substances, including proteins or polysaccharides. Such microparticles enable strategic manipulation of variables including total dose of drug and kinetics of its release. Microparticles can be injected efficiently into the arterial or venous wall through a porous balloon catheter or a balloon over stent, and are retained in the vascular wall and the periadventitial tissue for at least about two weeks. Formulations and methodologies for local, intravascular site-specific delivery of therapeutic agents are discussed in Reissen et al. (Am. C'oll. Cardial. 1994; 23: 1234-1244), the entire contents of which are hereby incorporated by reference.

A composition according to the invention may also comprise a hydrogel which is prepared from any biocompatible or non-cytotoxic (homo or hetero) polymer, such as a hydrophilic polyacrylic acid polymer that can act as a drug absorbing sponge. Such polymers have been described, for example, in application WO93/08845, the entire contents of which are hereby incorporated by reference. Certain of them, such as, in particular, those obtained from ethylene and/or propylene oxide are commercially available.

In the use of compounds according to the invention for treating atherosclerosis, or a condition related thereto, the compounds according to the invention can be administered in different ways. For the treatment of atherosclerosis, the compounds of the invention are administered directly to the blood vessel wall by means of an angioplasty balloon, which is coated with a hydrophilic film (for example a hydrogel) which is saturated with the compound, or by means of any other catheter containing an infusion chamber for the compound, which can thus be applied in a precise manner to the site to be treated and allow-the compound to be liberated locally and efficiently at the location of the cells to be treated. This method of administration advantageously makes it possible for the compound to contact quickly the cells in need of treatment.

Advantageously, the hydrogel is introduced at the desired intravascular site by coating a catheter, for example a balloon catheter, and delivery to the vascular wall, preferably at the time of angioplasty. In a particularly advantageous manner, the saturated hydrogel is introduced at the site to be treated by means of a balloon catheter. The balloon may be chaperoned by a protective sheath as the catheter is advanced toward the target vessel, in order to minimize drug washoff after the catheter is introduced into the bloodstream.

Another embodiment of the invention provides for a compound according to the invention to be administered by means of perfusion balloons. These perfusion balloons, which make it possible to maintain a blood flow and thus to decrease the risks of ischaemia of the myocardium, on inflation of the balloon, also enable the compound to be delivered locally at normal pressure for a relatively long time, more than twenty minutes, which may be necessary for its optimal action. Alternatively, a channeled balloon catheter ("channeled balloon angioplasty catheter", Mansfield Medical, Boston Scientific Corp., Watertown, Mass.) may be used. The latter consists of a conventional balloon covered with a layer of 24 perforated channels, which perfuse via an independent lumen through an additional infusion orifice.

Various types of balloon catheters, such as double balloon, porous balloon, microporous balloon, channel balloon, balloon over stent and hydrogel catheter, all of which may be used to practice the invention, are disclosed in Reissen et al. (1994), the entire contents of which are hereby incorporated by reference.

The use of a perfusion balloon catheter is especially advantageous, as it has the advantages of both keeping the balloon inflated for a longer period of time by retaining the properties of facilitated sliding and of site-specificity of the hydrogel are gained simultaneously.

Another aspect of the present invention relates to a pharmaceutical composition comprising a compound according to the invention and poloxamer, such as Poloxamer 407 is a non-toxic, biocompatible polyol, commercially available (BASF, Parsippany, N.J.).

A poloxamer impregnated with a compound according to the invention may be deposited directly on the surface of the tissue to be treated, for example during a surgical intervention. Poloxamer possesses essentially the same advantages as hydrogel while having a lower viscosity.

The use of a channel balloon catheter with a poloxamer impregnated with a compound according to the invention is especially advantageous. In this case, the advantages of both keeping the balloon inflated for a longer period of time while retaining the properties of facilitated sliding, and of site specificity of the poloxamer, are gained simultaneously.

The percentage of compound of formula I, II, III, or IV in the compositions used in the present invention may be varied, it being necessary that it should constitute a proportion such that a suitable dosage shall be obtained. Obviously, several unit dosage forms may be administered at about the same time. A dose employed may be determined by a physician or qualified medical professional, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 10, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

The compound of formula I, II, III, or IV used in the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the compound of formula I, II, III, or IV may be administered 1 to 4 times per day. Of course, for other patients, it will be necessary to prescribe not more than one or two doses per day.

The following non-limiting examples set forth hereinbelow illustrate certain aspects of the invention.

EXAMPLES

Example 1

Synthesis of 1,5-disubstituted DOPs (for DOP101-104)

Amide 1.0 gram was suspended in 5 ml DMF-dimethylacetal at room temperature and heat to reflux for two hours, thin layer chromatography (TLC) indicated the reaction was finished. After the solvent was evaporated, the residue was dissolved in 10 ml acetic acid. Next, 1.0 equivalent hydrazine chloride salt was added at room temperature. The solution was stirred at 95° C. until TLC confirmed that the reaction was finished. After the solution was cooled to room temperature, sodium hydroxide cold solution was dropped in to neutralize the solution and extracted by chloroform. Compounds DOP101 and DOP103 were purified by column chromatography. The structures of these compounds are as follows:

1-(4-tert-butyl-phenyl)-5-(3-methoxyl-phenyl)-1,2,4-triazole (DOP 101)

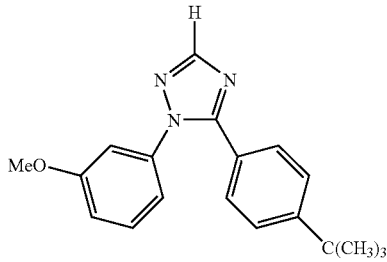

The following physical data was obtained for DOP101: $^1$H NMR (300 Hz, CDCl$_3$), δ: 1.32 (s, 9H), 3.64 (s, 3H), 3.83 (s, 1H), 6.91 (d, J=7 Hz, 1H), 7.04 (t, J=6 Hz, 1H), 7.22 (d, J=8 Hz, 1H), 7.26 (d, J=8 Hz, 2H), 7.42 (d, J=7 Hz, 2H), 8.06 (s, 1H).

1-(3-methoxyl-phenyl)-5-(4-tert-butyl-phenyl)-1,2,4-triazole (DOP 103)

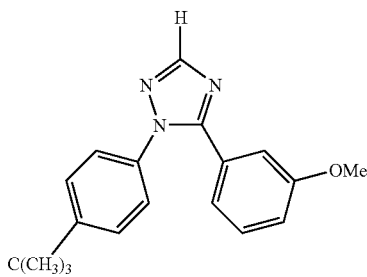

The following physical data was obtained for DOP103: $^1$H NMR (300 Hz, CDCl$_3$), δ: 1.29 (s, 9H), 3.75 (s, 3H), 3.87 (s, 1H), 6.90-6.97 (m, 2H), 7.28-7.43 (m, 3H), 7.43 (d, J=8 Hz, 2H), 8.06 (s, 1H).

The methoxy group was then hydrolyzed by boron tribromide in anhydrous dichloromethane (DCM) under standard conditions. Compounds DOP102 and DOP104 were purified by column chromatography. The structures of these compounds are as follows:

1-(4-tert-butyl-phenyl)-5-(3-hydroxyl-phenyl)-1,2,4-triazole (DOP 102)

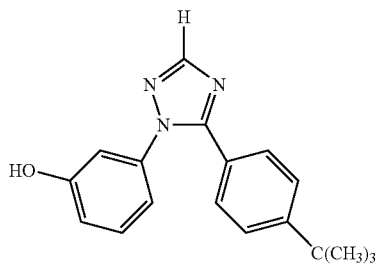

The following physical data was obtained for DOP102: $^1$H NMR (300 Hz, CDCl$_3$), δ: 1.32 (s, 9H), 6.75 (d, J=6 Hz, 1H), 6.86 (d, J=6 Hz, 1H), 7.12 (t, J=8 Hz, 1H), 7.26 (d, J=8 Hz, 2H), 7.27 (s, 1H), 7.41 (d, J=7 Hz, 2H), 8.04 (s, 1H), 8.09 (s, 1H).

(1-(3-hydroxyl-phenyl)-5-(4-tert-butyl-phenyl)-1,2,4-triazole (DOP 104)

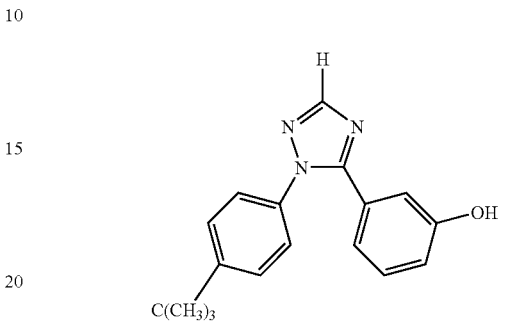

The following physical data was obtained for DOP104: $^1$H NMR (300 Hz, CDCl$_3$), δ: 1.28 (s, 9H), 6.81 (d, J=1 Hz, 1H), 6.87 (d, J=3 Hz, 1H), 6.88 (s, 1H), 7.23 (t, J=9 Hz, 1H), 7.33 (d, J=4 Hz, 2H), 7.42 (d, J=5 Hz, 2H), 7.98 (s, 1H).

Example 2

Synthesis of 1,3,5-trisubstituted DOPs (for DOP105-110)

Anisidine 20 mmol was dissolved in 50 ml hydrochloride solution and cooled to 5° C., and 1.0 equivalent sodium nitrite was added at 0-5° C. Five minutes later, 1.0 equivalent of ethyl-2-chloroacetoacetate 1.0 equivalent was dropped and controlled the temperature <1° C. After TLC indicating that the reaction was finished, the product was extracted by chloroform and purified by column chromatography.

The chloro-compound was dissolved in THF and ammonia gas was introduced by bubbling through the THF solution to give amidrazone in 100% yield. The amidrazone was dissolved in toluene and different acid was added in following 1.2 equivalent DCC as coupling reagent to give the cyclization product with ethyl ester substitution group, and the ester was reduced to ethanol using lithium aluminum hydride as reduction reagent. By using the Mitsonobu reaction, the ethyl alcohol group was converted to iodide under standard condition and the final product was achieved by refluxing with amine under nitrogen. The hydrolysis of methoxy group was produced using boron tribromide as indicated above. All of the DOPs were purified by flash column chromatography.

The following physical data was obtained for 3-[5-(3-tert-Butyl-phenyl)-3-dimethylaminomethyl-[1,2,4,]triazole-1-yl]-phenol (DOP 106): $^1$H NMR (300 Hz, CDCl$_3$), δ: 1.11 (s, 9H), 2.13 (s, 6H), 3.57 (s, 1H), 6.16 (s, 1H), 6.85 (d, J=6 Hz, 1H), 6.93 (d, J=6 Hz, 1H), 7.08-7.18 (m, 3H), 7.24-7.32 (m, 3H).

The following physical data was obtained for [5-(4-tert-Butyl-phenyl)-1-(3-methoxy-phenyl)-1H-[1,2,4]triazole-3-ylmethyl]-dimethyl-amine (DOP 107): $^1$H NMR (300 Hz, CDCl$_3$), δ: 1.29 (s, 9H), 2.41 (s, 6H), 3.67 (s, 2H), 3.75 (s, 3H), 6.93 (t, J=7 Hz, 2H), 7.35-7.34 (m, 4H), 7.45 (d, J=8 Hz, 2H).

The following physical data was obtained for 3-[5-(4-tert-Butyl-phenyl)-3-dimethylaminomethyl-[1,2,4,]triazole-1-yl]-phenol (DOP 108): $^1$H NMR (300 Hz, CDCl$_3$), δ: 1.25 (s, 9H), 2.21 (s, 6H), 3.57 (s, 2H), 6.26 (s, 1H), 6.83 (d, J=5 Hz, 2H), 6.89 (d, J=4 Hz, 2H), 7.22-7.26 (m, 4H).

The following physical data was obtained for [5-(2,4-Dimethyl-phenyl)-1-(3-methoxy-phenyl)-1H-[1,2,4]triazole-3-ylmethyl]-dimethyl-amine (DOP 109): $^1$H NMR (300 Hz, CDCl$_3$), δ: 2.01 (s, 3H), 2.31 (s, 3H), 2.42 (s, 6H), 3.64 (s, 3H), 3.71 (s, 2H), 6.77-6.82 (m, 3H), 6.98 (d, J=2 Hz, 2H), 7.13-7.17 (m, 2H).

The following physical data was obtained for 3-[5-2,4-Dimethyl-phenyl)-3-dimethylaminomethyl-[1,2,4,]triazole-1-yl]-phenol (DOP 110): $^1$H NMR (300 Hz, CDCl$_3$), δ: 2.96 (s, 3H), 2.28 (s, 3H), 2.40 (s, 6H), 3.73 (s, 2H), 6.54 (s, 1H), 6.64 (d, J=8 Hz, 1H), 6.71 (d, J=5 Hz, 1H), 6.93-6.96 (m, 2H), 7.01-7.08 (m, 3H).

Example 3

Evaluation of Biological Activity

Receptor binding assay: Cell membrane preparations were obtained from HEK 293-stable transfectants expressing either the murine δ or μ or the human κ receptor. Opioid receptor binding assays were conducted in duplicate on membrane preparations that had been resuspended in 50 mM Tris-HCl, pH 7.5, utilizing [$^3$H]DPDPE, [$^3$H]DAMGO and [$^3$H]U69593 as radioligand for δ, μ, and κ respectively and 10 μM cyclazocine to define non-specific binding. Following a 1 hour incubation on ice, binding assays were terminated by filtration through Whatman GF/B filters. Filters were soaked in Ecoscint liquid scintillation solution (National Diagnostics, Manville, N.J.) and filter-bound radioactivity was measured using a Packard Tri-Carb 2100 TR liquid scintillation analyzer. Receptor binding data was analyzed by non-linear regression of saturation and competition curves using Prisim 3.0 software (GraphPad Software, San Diego, Calif.). Protein concentrations were determined with the Bio-Rad protein using bovine serum albumin as the standard.

Receptor down regulation assays: HEK 293 cells expressing the FLAG-tagged δ-receptor were grown to near confluence in 100 mm dishes in DMEM media supplemented with 10% fetal calf serum and 0.25 mg/ml G418. Media was replaced with serum-free media prior to overnight incubation with 10 μM or 20 μM of DOP or control compound. Media was aspirated and cell washed twice with cold PBS. Cell homogenates were collected and further washed trice with 50 mM TRIS-HCl, pH 7.5. Protein concentration was measured using Bio-Rad Bradford reagent and equal amount of protein (50 μg) was used for binding assay. Binding assays were performed using [$^3$H]diprenorphine as the radioactive ligand. Binding assays were conducted as described above.

The apparent IC$_{50}$ values are close to those for the potent delta-selective agonist SNC80:

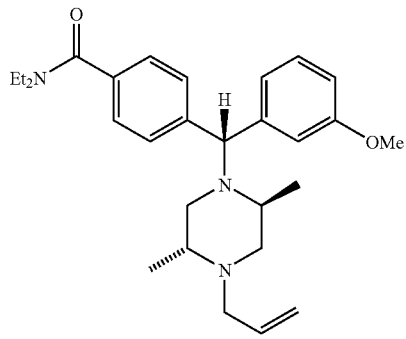

and the analogous AR-M390 and SL-3111:

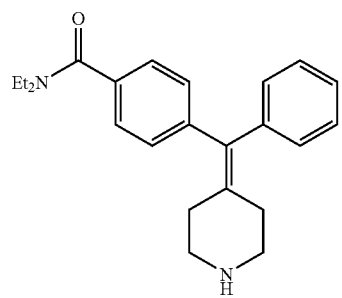

AR-M390

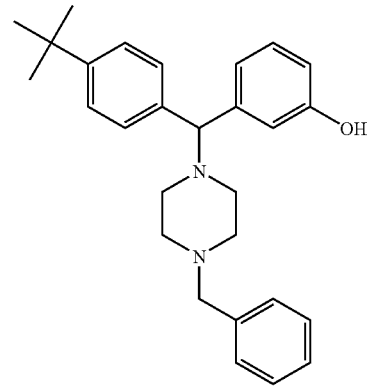

SL-3111 as set forth in Table I:

TABLE I

Binding affinities for and function at the opioid receptors of representative compounds of Formula I. Literature values for SNC80, AR-M390, and SL-3111 are provided for comparison.

| Compound | IC$_{50}$ (nM) | | | Selectivity | | Function at |
| | δ$^a$ | μ$^b$ | κ$^c$ | μ/δ | κ/δ | δ |
| --- | --- | --- | --- | --- | --- | --- |
| DOP106 | 48.9 ± 8.30 | 2447 ± 661 | 341 ± 20 | 50 | 7 | Agonist |
| DOP108 | 5.84 ± 1.24 | >10000 | 3851 ± 311 | >1712 | 659 | Agonist |
| DOP110 | 273 ± 82 | 2435 ± 372 | 351 ± 95 | 8.9 | 1.3 | Agonist |
| SNC80 | 0.73 ± 0.05 | 6066 ± 478 | 3601 ± 523 | 8309 | 4933 | Agonist |

TABLE I-continued

Binding affinities for and function at the opioid receptors of representative compounds of Formula I. Literature values for SNC80, AR-M390, and SL-3111 are provided for comparison.

| Compound | IC$_{50}$ (nM) | | | Selectivity | | Function at |
| --- | --- | --- | --- | --- | --- | --- |
| | $\delta^a$ | $\mu^b$ | $\kappa^c$ | $\mu/\delta$ | $\kappa/\delta$ | $\delta$ |
| AR-M390d | 0.89 ± 0.23 | 3800 ± 172 | 7470 ± 606 | 4370 | 8590 | Agonist |
| SL-3111e | 8.4 ± 1.6 | 17000 ± 30000 | N/A | 2020 | N/A | Agonist |

[a] Inhibitory effect to [3H]DPDPE in rat HEK 293 cell membrane stably expressing the rat delta receptor.
[b] Inhibitory effect to [3H]DAMGO HEK 293 cell membrane stably expressing the rat mu receptor.
[c] Inhibitory effect to [3H]U69593 HEK 293 cell membrane stably expressing the human kappa receptor.
[d] Inhibitory effect to [125I][D-Ala2]deltorphin II, [125I]FK33824 [125I][D-Pro10]dynorphin A in $\delta$, $\mu$ and $\kappa$ human brain membranes.
[e] Inhibitory effect to [3H]p-Cl-DPDPE and [3H]DAMGO in $\delta$ and $\mu$ rat brain membranes.

In particular, Compound DOP108 exhibited exceptional binding affinity (IC$_{50}$=5.84 nM, FIG. 1) and selectivity for $\delta$ over $\mu$ and $\kappa$ (selectivity ratio $\mu/\delta$=>1712, $\kappa/\delta$=659). Compounds tested thus far in this series behave functionally at the $\delta$ receptor as strong agonists (FIG. 2) and are non-toxic to cells at concentrations up to 20 $\mu$M.

Additional comparisons of the representative subject DOPs with SNC80 and various analogs are also set forth in Table II:

TABLE II

| Compound | MW | NCC | ClogP | MV (Å3) | SA (Å2) | PSA (Å2) | HBD | HBA |
| --- | --- | --- | --- | --- | --- | --- | --- | --- |
| DOP105 | 350.5 | 0 | 4.69 | 1.1*103 | 645.3 | 35.35 | 0 | 5 |
| DOP106 | 350.5 | 0 | 4.69 | 1.1*103 | 627.4 | 61.92 | 1 | 5 |
| DOP107 | 350.5 | 0 | 4.69 | 1.1*103 | 662.2 | 34.42 | 0 | 5 |
| DOP108 | 350.5 | 0 | 4.69 | 1.1*103 | 661.1 | 67.67 | 1 | 5 |
| DOP109 | 322.4 | 0 | 3.56 | 1.0*103 | 639.7 | 30.81 | 0 | 5 |
| DOP110 | 322.4 | 0 | 3.56 | 1.0*103 | 633.9 | 65.95 | 1 | 5 |
| SNC80 | 449.6 | 3 | 4.93 | 1.4*103 | 814.1 | 38.89 | 0 | 5 |
| AR-M390 | 348.5 | 0 | 3.53 | 1.1*103 | 665.3 | 59.65 | 1 | 3 |
| SL-3111 | 414.6 | 1 | 6.68 | 1.3*103 | 752.7 | 53.04 | 1 | 3 |
| DPI 3290 | 487.6 | 3 | 5.20 | 1.4*103 | 838.4 | 85.23 | 1 | 5 |

MW: molecular weight;
NCC: number of chiral carbons;
MV: molecular volume;
SA: surface area;
PSA: polar surface area;
HBD: hydrogen-bond donor;
HAD: hydrogen-bond acceptor.

Further, a binding affinity summary of representative compounds of Formula II expressed in terms of IC$_{50}$ for each receptor is set forth in Table III:

TABLE III

| Compound | $\delta$ (nM) | $\mu$ (nM) | $\kappa$ (nM) |
| --- | --- | --- | --- |
| DST8S | 2778 | 991 | 2134 |
| DST10S | 114 | 118 | 23 |

The results of Table III indicate that DST10S is a particularly strong agonist at the kappa opioid receptor (IC$_{50}$=23 nM) and a moderate to strong antagonist at both the mu opioid receptor (IC$_{50}$=118 nM) and the delta opioid receptor (IC$_{50}$=114 nM).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A compound of Formula I:

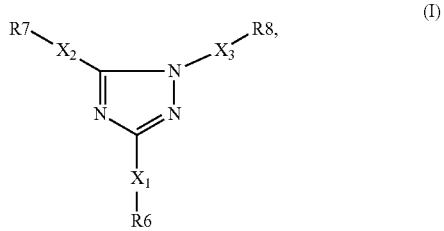

wherein
X$_1$ is a bond or a saturated or unsaturated alkylene group;
X$_2$ and X$_3$ are bonds;
R$_6$ is CH$_2$N(CH$_3$)$_2$; and R$_7$ and R$_8$ are independently selected from the group consisting of m-tert-butyl phenyl, p-tert-butyl phenyl, 3,4-dimethyl phenyl, phenol, and methoxy phenyl; or a pharmaceutically acceptable salt of said compound.

2. The compound of claim 1, wherein the compound comprises 0 to 2 chiral centers.

3. The compound of claim 1, wherein the compound is achiral.

4. A pharmaceutical composition comprising a pharmaceutically effective amount of the compound according to claim 1 and a pharmaceutically acceptable carrier.

5. The composition of claim 4 further comprising a μ-agonist.

6. The composition of claim 5, wherein the μ-agonist comprises morphine or fentanyl.

7. A method for diagnosing or treating a condition mediated by an opioid receptor, said method comprising administering an effective amount of the compound of claim 1 to a patient in need thereof.

8. The method of claim 7, wherein said condition is selected from the group consisting of pain, inflammation, and depression.

* * * * *